US010012648B2

(12) United States Patent
Paintsil et al.

(10) Patent No.: US 10,012,648 B2
(45) Date of Patent: Jul. 3, 2018

(54) PLASMA CYTOCHROME C AS A BIOMARKER FOR MITOCHONDRIAL TOXICITY DURING ANTIRETROVIRAL THERAPY

(71) Applicant: Yale University, New Haven, CT (US)

(72) Inventors: Elijah Paintsil, Hamden, CT (US); Allison Langs-Barlow, Greenvale, NY (US)

(73) Assignee: Yale University, New Haven, CT (US)

( * ) Notice: Subject to any disclaimer, the term of this patent is extended or adjusted under 35 U.S.C. 154(b) by 195 days.

(21) Appl. No.: 14/725,835

(22) Filed: May 29, 2015

(65) Prior Publication Data
US 2015/0346213 A1    Dec. 3, 2015

Related U.S. Application Data

(60) Provisional application No. 62/007,121, filed on Jun. 3, 2014.

(51) Int. Cl.
*A61K 39/21* (2006.01)
*G01N 33/569* (2006.01)

(52) U.S. Cl.
CPC . *G01N 33/56988* (2013.01); *G01N 33/56983* (2013.01); *G01N 2333/80* (2013.01)

(58) Field of Classification Search
None
See application file for complete search history.

(56) References Cited

U.S. PATENT DOCUMENTS

2006/0183176 A1    8/2006  Endo et al.
2012/0129188 A1*   5/2012  Gazmuri ............ A61K 38/1816
                                                                     435/7.9

OTHER PUBLICATIONS

Ow et al. Cytochrome c: functions beyond Respiration. Nat. Rev. 2008; 9: 532-542.*
Lewis and Dalakas, Mitochondrial toxicity of antiviral drugs. Nat. Med. 1995; 1(3): 417-422.*
Dias and Bailly, Drugs targeting mitochondrial functions to control tumor cell growth. Biochem. Pharmacol. 2005; 70: 1-12.*
Porceddu et al. Prediction of Liver Injury Induced by Chemicals in Human With a Multiparametric Assay on Isolated Mouse Liver Mitochondria. Toxicolog. Sci. 2012; 129(2): 332-345.*

(Continued)

*Primary Examiner* — Janet L Andres
*Assistant Examiner* — Stuart W Snyder
(74) *Attorney, Agent, or Firm* — Saul Ewing Arnstein & Lehr LLP; Kathryn Doyle (57) ABSTRACT

The present invention relates to the discovery that measurement of the level of cytochrome c (Cyt-C) in the plasma can be used as a diagnostic signature to predict antiretroviral therapy (ART) toxicity in human immunodeficiency virus (HIV) infected patients. Thus, in various embodiments described herein, the methods of the invention relate to methods of diagnosing a HIV patient with ART toxicity, methods of predicting a patient's risk of having or developing toxicity for ART, methods of assessing if a patient will benefit from a change in the treatment strategies by adjusting the dosage and/or changing the medication or even terminating of ART, and methods of predicting antiretroviral drugs propensity for causing mitochondrial toxicity. Furthermore, the invention encompasses a diagnostic kit for carrying out the aforementioned methods.

22 Claims, 3 Drawing Sheets

(56) References Cited

OTHER PUBLICATIONS

Chung et al. Highly Active Antiretroviral Therapy (HAART) versus Zidovudine/Nevirapine Effects on Early Breast Milk HIV-1 RNA: A Phase II Randomized Clinical Trial. Antivir. Ther. 2008; 13(6): 799-807.*
Zhang et al. The Chinese free antiretroviral treatment program: challenges and responses. AIDS, 2007; 21(suppl 8):S143-S148.*
Carr and Cooper, Adverse effects of antiretroviral therapy. Lancet 2000; 356: 1423-30.*
Gardner, et al., "HIV treatment and associated mitochondrial pathology: review of 25 years of in vitro, animal, and human studies", Toxicol Pathol. 42(5), Jul. 2014, 811-822.
Maggi, et al., "Early markers of tubular dysfunction in antiretroviral-experienced HIV-infected patients treated with tenofovir versus abacavir", AIDS Patient Care STDS. 26(1), Jan. 2012, 5-11.
Miller, et al., "Cytochrome c: a non-invasive biomarker of drug-induced liver injury", J Appl Toxicol. 28(7), Oct. 2008, 815-828.
Renz, et al., "Rapid extracellular release of cytochrome c is specific for apoptosis and marks cell death in vivo", Blood. 98(5), Sep. 1, 2001, 1542-1548.

* cited by examiner

PLASMA CYTOCHROME C AS A BIOMARKER FOR MITOCHONDRIAL TOXICITY DURING ANTIRETROVIRAL THERAPY

CROSS-REFERENCE TO RELATED APPLICATIONS

The present application claims priority under 35 U.S.C. § 119(e) to U.S. Provisional Application No. 62/007,121, filed Jun. 3, 2014, which application is hereby incorporated by reference in its entirety herein.

STATEMENT REGARDING FEDERALLY SPONSORED RESEARCH OR DEVELOPMENT

This invention was made with government support under grant K08AI074404 awarded by the National Institute of Allergy and Infectious Diseases at the National Institutes of Health. The government has certain rights in the invention.

BACKGROUND OF THE INVENTION

Human Immunodeficiency Virus (HIV) is a retrovirus that infects and invades cells of the immune system and causes acquired immunodeficiency syndrome (AIDS). HIV breaks down the body's immune system and renders the patient susceptible to life-threatening opportunistic infections and cancers. The immune defect appears to be progressive and irreversible, with a high mortality rate that approaches 100% over several years.

The management of HIV/AIDS normally includes the use of multiple antiretroviral drugs in an attempt to control HIV infection. Antiretroviral therapy (ART) includes several classes of antiretroviral agents that act on different stages of the HIV life-cycle: (a) entry inhibitors interfere with binding, fusion and entry of HIV-1 to the host cell by blocking one of several targets; (b) nucleoside and nucleotide reverse transcriptase inhibitors (NRTI and NTRTI) are nucleoside and nucleotide analogues which inhibit reverse transcription; (c) non-nucleoside reverse transcriptase inhibitors (NNRTI) inhibit reverse transcriptase; (d) integrase nuclear strand transfer inhibitors (INSTI) inhibit the viral enzyme integrase, which is responsible for integration of viral DNA into the DNA of the infected cell; and (e) protease inhibitors (PI) block the viral protease enzyme necessary to produce mature virions upon budding from the host membrane (www.aidsinfo.nih.gov/guidelines).

The use of multiple drugs that act on different viral targets is known as highly active antiretroviral therapy (HAART). HAART was introduced in 1996 and involves various combinations of HIV inhibitors including, but not limited to, NRTI, NNRTI and PI (Schmit et al., The Journal of Infectious Diseases, 1996, 174 (5): 962-8). HAART has been effective in reducing mortality and progression of HIV-1 to AIDS and in improving patient quality of life.

Although ART has decreased morbidity and mortality for HIV, long-term therapy is associated with toxicity (Gardner et al., Toxicol Pathol, 2013—Review). As ART use increases worldwide, the need for toxicity monitoring has become imperative. The 2013 UNAIDS report on the global AIDS epidemic highlights ART pharmacovigilance as a priority for HIV care programs. The prevalence of all ART adverse events is reported to be 47% for clinical and 27% for laboratory manifestations, with 9% to 16% of these leading to changes in medication, hospitalization, chronic disability, or death (Fellay et al., Lancet, 2001, 358:1322-1327). Prevalence data for ART toxicity in children are scarce, although one study of 3936 HIV-infected children <5 years old living in low resource settings found that 3.8% had to switch to a second-line drug regimen within the first 36 months of ART due to medication toxicity (Sauvageot et al., Pediatrics, 2010, 125:e1039-1047).

Mitochondria organelles are found in every cell of the human body except red blood cells and play a major role in energy production and glucose and fat metabolism. Early effects of mitochondrial toxicity include a decrease in energy production and an increased production of lactate. Mitochondrial toxicity has been suggested as a common pathway for a variety of nucleoside-related adverse effects, including asymptomatic hyperlactatemia or varying degrees of fatigue, shortness of breath, nausea, vomiting, abdominal pain, weight loss, and even severe fatal lactic acidosis with severe liver steatosis. Also, cardiomyopathy, peripheral neuropathy, pancreatitis, hepatotoxicity, lipoatrophy and lipodystrophy have been attributed to underlying nucleoside-related mitochondrial toxicity (Birkus et al., Antimicrob Agents Chemother, 2002, 46(3):716-23; Fellay et al., Lancet, 2001, 358:1322-1327 and Renner et al., J Int AIDS Soc 2013, 16:18024).

In general, clinical manifestations of ART-induced mitochondrial toxicity can affect nearly any organ system (Gardner et al., Toxicol Pathol, 2013—Review). The underlying mechanism for mitochondrial toxicity, in the case of nucleoside reverse transcriptase inhibitors (NRTI), is attributed to inhibition of polymerase gamma, the key enzyme responsible for mitochondrial DNA replication (Johnson et al. J Biol Chem. 2001, 276:40847-57; Martin et al., Antimicrob Agents Chemother, 1994; 38:2743-9; Kohler et al., Environ Mol Mutagen, 2007, 48:166-172). However, NRTI, as well as other classes of antiretroviral agents such as non-nucleoside reverse transcriptase inhibitors and protease inhibitors, have also been reported to increase rates of apoptosis (Braga et al., BMC Gastroenterol 2010, 10:90), whether as a result of or in addition to mitochondrial damage is not certain. Outside of clearly defined clinical manifestations, diagnosis of mitochondrial toxicity is difficult given that there is no gold standard test. A combination of clinical symptoms, laboratory testing, and imaging studies, culminating in tissue biopsy to look for mitochondrial damage is deemed to be the most accurate method (Haas et al., Pediatrics 2007, 120:1326-1333), though it is cost-prohibitive and invasive. Thus, a "trial and error" approach to ART toxicity, in which medications are stopped or switched to see if the clinical manifestations resolve, has become commonplace. This practice favors the emergence of drug-resistant strains of HIV (Arnedo-Valero et al., Clin Infect Dis 2005, 41:883-890) and could lead to inappropriate use of second-line medications, especially in resource-limited settings.

Cytochrome C (Cyt-C) is a protein made from nuclear DNA as apocytochrome c, which is then shuttled across the mitochondrial outer membrane and transformed to a heme-containing, water soluble protein of approximately 12 kDa (Kulikov, et al., Cell Mol Life Sci, 2012, 69(11): p. 1787-97). It acts as a substrate in oxidative phosphorylation. Its release into the cytosol of the cell is a pro-apoptotic signal (Ow et al., Nat Rev Mol Cell Biol, 2008, 9(7): p. 532-42). In vivo, Cyt-C has been detected extracellularly during pro-apoptotic states (Renz A et al., Blood, 2001, 98:1542-1548). It has also been identified in circulation in experimental models of drug induced renal and hepatic toxicity (Small et al., Expert Opin Drug Metab Toxicol, 2012, 8:655-664; Miller et al., J Appl Toxicol, 2008, 28:815-828). Cyt-C can be detected in serum and/or plasma using a commercial enzyme linked immunosorbant assay (ELISA) (Marenzi et al., Am J Cardiol, 2010, 106(10): p. 1443-9; Dincer et al., Clin Invest Med, 2009, 32(4): p. E266-70; Barczyk et al., Int J Cancer, 2005, 116(2): p. 167-'73; Dincer et al., J Thromb Thrombolysis, 2010, 29(1): p. 41-5).

There is a need in the art for methods for detecting and quantifying ART-induced mitochondrial toxicity. Furthermore, there is a need in the art for a non-invasive, cost-effective diagnostic test with strong sensitivity and selectivity so as to inform clinicians on the status of the patient undergoing ART, in order to prevent unnecessary interruptions in ART, guide the use of second-line regimens and thus provide the best treatment modalities. The present invention satisfies these needs.

SUMMARY OF THE INVENTION

The present invention provides a method for detecting antiretroviral drug toxicity in a subject having a viral infection. The method comprises determining the level of an apoptotic protein in a sample from the subject, comparing the level of an apoptotic protein in the sample from the subject relative to a baseline level in a reference wherein an increase in the level of the apoptotic protein in the sample when compared with the level of the same apoptotic protein in the reference is indicative of drug toxicity, and wherein when drug toxicity is indicated, a modification in the drug treatment modality is recommended to the subject.

In another aspect, the invention includes a method for assessing toxicity associated with antiretroviral therapy (ART) in a subject having a viral infection as a mean to modify or terminate ART treatment. The method comprises determining the level of an apoptotic protein in a sample from the subject, and comparing the level of an apoptotic protein in the sample from the subject relative to a baseline level in a reference, wherein an increase in the level of the apoptotic protein in the sample when compared with the level of the same apoptotic protein in the reference is an indication of whether or not ART treatment should be modified or terminated.

The invention further includes a kit comprising an antibody to Cytochrome c (Cyt-C) and instructions for use thereof. The instructions of the kit comprise measuring the level of Cyt-c in a sample from a subject having a viral infection, providing indication on presence or absence of antiretroviral therapy (ART) toxicity, and providing recommendation of whether or not ART treatment should be modified or terminated in the subject.

In some embodiments, the toxicity is a mitochondrial toxicity. In some embodiments, the apoptotic protein is a mitochondrial protein. In other embodiments, the mitochondrial protein is Cytochrome c (Cyt-C).

In some embodiments, the viral infection is a retroviral infection. In other embodiments, the retroviral infection is a human immunodefiency virus (HIV) infection.

In yet other embodiments, the antiretroviral drug is at least one selected from the group consisting of nucleotide reverse transcriptase inhibitor (NTRTI), nucleoside reverse transcriptase inhibitor (NRTI), protease inhibitor (PI) and integrase nuclear strand transfer inhibitor (INSTI). In yet further embodiments, the antiretroviral drug is a highly active antiretroviral therapy (HAART).

In some embodiments, determining the level of the Cyt-C is accomplished using at least one technique selected from the group consisting of ELISA, spectrophotometry and protein microarray.

In some embodiments, the sample is a blood sample. In other embodiments, the blood sample is a plasma sample.

In some embodiments, the subject is a mammal. In other embodiments, the mammal is a human. In yet other embodiments, the human is a child.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

The present invention relates to the discovery that measurement of the level of plasma Cytochrome c (Cyt-C) can be used as a diagnostic signature to detect antiretroviral therapy (ART) toxicity in human immunodeficiency virus (HIV) infected patients. Thus, in various embodiments described herein, the methods of the invention relate to methods of diagnosing a HIV patient with toxicity for ART, methods of predicting a patient's risk of having or developing toxicity for ART and methods of assessing if a patient requires an adjustment of dosage and/or medication or even termination of ART, and methods of predicting antiretroviral drugs propensity for causing mitochondrial toxicity. Furthermore, the invention encompasses a diagnostic kit for carrying out the aforementioned methods.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0, 1% from the specified value, as such variations are appropriate to perform the disclosed methods.

The terms "anti-retroviral" agent, drug, preparation, composition and the like, as used herein, means that the agent, preparation, composition and the like, is capable of controlling or inhibiting the proliferation or multiplication of the retrovirus in a susceptible host.

As used herein, the term "retrovirus" means a single-stranded RNA virus characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants.

The term "apoptosis", as used herein, means an active process, involving the activation of a preexisting cellular pathway, induced by an extracellular or intracellular signal, causing the death of the cell. In particular, the cell death involves nuclear fragmentation, chromatin condensation, and the like, in a cell with an intact membrane.

"Antiretroviral therapy" or "antiretroviral drug" are used interchangeably herein to refer to a nucleoside reverse transcriptase inhibitor, a fusion inhibitor, a protease inhibitor, and a non-nucleoside reverse transcriptase inhibitor, collectively known as HAART. Such antiretroviral therapy regimens include, but are not limited to, one or a combination of the following drugs: COMBIVIR™ (lamivudine and zidovudine), EMTRIVA™ (FTC, emtricitabine), EPIVIR™ (lamivudine, 3TC), HIVID™ (zalcitabine, ddC, dideoxycitidine), RETROVIR™ (zidovudine, AZT, azidothymidine, ZDV), TRIZIVIR™ (abacavir, zidovudine, lamivudine), VIDEX™ (didanosine, ddI, dideoxyinosine), VIDEX EC™ (enteric coated didanosine), VIREAD™ (tenofovir disoproxil fumarate), ZERIT™ (stavudine, d4T), ZIAGEN™ (abacavir), AGENERASE™ (amprenavir), CRIXIVAN™ (indinavir, IDV, MK-639), FORTOVASE™ (saquinavir), INVIRASE™ (saquinavir mesylate, SQV), KALETRA™ (lopinavir and ritonavir), NORVIR™ (ritonavir, ABT-538), REYATAZ™ (atazanavir sulfate), VIRACEPT™ (nelfinavir mesylate, NFV), FUZEON™ (enfuvirtide, T-20), RESCRIPTOR™ (delavirdine, DLV), SUSTIVA™ (efavirenz) and VIRAMUNE™ (nevirapine, BI-RG-587).

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, to "treat" means reducing the frequency with which symptoms of a disease, disorder, or adverse condition, and the like, are experienced by a subject.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

The term, "polynucleotide" includes cDNA, RNA, DNA/RNA hybrid, anti-sense RNA, siRNA, miRNA, snoRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have a N-terminal and a C-terminal. The N-terminal will have an amino group, which may be free (i.e., as a NH2 group) or appropriately protected (for example, with a BOC or a Fmoc group). The C-terminal will have a carboxylic group, which may be free (i.e., as a COOH group) or appropriately protected (for example, as a benzyl or a methyl ester). A cyclic peptide does not have free N- or C-terminal, since they are covalently bonded through an amide bond to form the cyclic structure. Amino acids may be represented by their full names (for example, leucine), 3-letter abbreviations (for example, Leu) and 1-letter abbreviations (for example, L). The structure of amino acids and their abbreviations may be found in the chemical literature, such as in Stryer, "Biochemistry", 3rd Ed., W. H. Freeman and Co., New York, 1988. tLeu represents tert-leucine. neo-Trp represents 2-amino-3-(1H-indol-4-y])-propanoic acid. DAB is 2,4-diaminobutyric acid. Orn is ornithine. N-Me-Arg or N-methyl-Arg is 5-guanidino-2-(methylamino)pentanoic acid.

"Sample" or "biological sample" as used herein means a biological material from a subject, including but is not limited to organ, tissue, exosome, blood, plasma, saliva, urine and other bodily fluids such as interstitial fluid, lymph, gastric juices, bile, sweat, tear fluid and brain and spinal fluids. A sample can be any source of material obtained from a subject.

The terms "subject", "patient", "individual", and the like are used interchangeably herein, and refer to any animal, or cells thereof whether in vitro or in situ, amenable to the methods described herein. In certain non-limiting embodiments, the patient, subject or individual is a human. Non-human mammals include, for example, livestock and pets, such as ovine, bovine, porcine, canine, feline and murine mammals. Preferably, the subject is human. The term "subject" does not denote a particular age or sex.

The term "child" refers to a subject of 18 years of age or younger. Particularly, this term refers to a subject of 18 months to 18 years of age.

The term "measuring" according to the present invention relates to determining the amount or concentration, preferably semi-quantitatively or quantitatively. Measuring can be done directly.

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

The term "biomarker" or "marker" as used herein refers to molecules such as a polynucleotide or a polypeptide, in an individual which are differentially present (i.e. present in increased or decreased levels) depending on presence or absence of a certain condition, disease, or complication. In particular, biochemical markers are gene expression products which are differentially present (e.g. through increased or decreased level of expression or turnover) in presence or absence of a certain condition, disease, or complication. The level of a suitable biomarker can indicate the presence or absence of a particular condition, disease, or risk, and thus allow diagnosis or determination of the condition, disease or risk.

As used herein, "mitochondrial toxicity" refers to any disorder that is directly or indirectly a result of, or caused by, malfunction of a mitochondrion in a cell. Mitochondrial toxicity is associated with a metabolic disorder in an individual. The metabolic disorder is drug-induced (e.g. phospholipidosis) or caused by inborn errors.

As used herein the term "amount" refers to the abundance or quantity of a constituent in a mixture.

The term "concentration" refers to the abundance of a constituent divided by the total volume of a mixture. The term concentration can be applied to any kind of chemical mixture, but most frequently it refers to solutes and solvents in solutions.

As used herein, the terms "reference," or "threshold" are used interchangeably, and refer to a value that is used as a constant and unchanging standard of comparison.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2, 7, 3, 4, 5, 5.3, and 6. This applies regardless of the breadth of the range.

Description

The present invention relates to the discovery that measurement of the level of cytochrome c (Cyt-C) in the plasma can be used as a diagnostic signature to predict antiretroviral therapy (ART) toxicity in human immunodeficiency virus (HIV) infected patients.

Methods of the Invention

The present invention is directed to a method for assessing whether a virus infected subject who is administered an antiretroviral drug is susceptible to drug toxicity. The method comprises determining the level of an apoptotic protein in a sample from a subject, and comparing the level of an apoptotic protein in the sample from the subject relative to a baseline level in a reference, whereby it is assessed whether the subject is experiencing drug toxicity. Thus, if a drug toxicity is indicated, a modification in the drug treatment modality is recommended.

In some embodiments, the subject has a retroviral infection. In other embodiments, the retroviral infection is human immunodefiency virus (HIV) infection.

In some aspects of the present invention, the apoptotic protein is Cytochrome c (Cyt-C).

In certain aspects of the present invention, the biomarker is detected in a sample comprising blood, serum, plasma or other bodily fluids sample, such as interstitial fluid, urine, whole blood, saliva, serum, lymph, gastric juices, bile, sweat, tear fluid and brain and spinal fluids. Bodily fluids may be processed or unprocessed prior to assessing the level of Cyt-C therein. In further aspects, the sample can be taken from a tissue culture or from the supernatant media of a tissue culture.

In the context of the present invention, the subject is or will be administered HAART, and, thus, is treated with ART when collecting the sample, or will be treated with ART after the sample has been collected. The daily dosage and method of administration of ART is based on the recommendations of the US Department of Health and Human Services Panel on Antiretroviral Guidelines for Adults and Adolescents (DHHS ART Guidelines, http://aidsinfo.nih.gov/content-files/AdultandAdolescentGL.pdf, 2011). In some embodiments, the nucleoside reverse transcriptase inhibitor is, but not limited to, Truvada, Atripla, Comivir, Epivir, Trizir. In certain embodiments, the subject has been administered ART for at least about one month, at least about three months, at least about six months, at least about twelve months, at least about one year, at least about two years prior to analysis of the sample.

In certain embodiments, the biomarker for ART toxicity is a peptide or polypeptide involved directly or indirectly in apoptosis. In other embodiments, the biomarker for ART toxicity is a mitochondrial biomarker that is a member of one of the following families: caspases, pro-/anti-apoptotic regulators, or oxidoreductases. More specifically, the mitochondrial biomarker can be a subunit of NADH dehydrogenase, a subunit of cytochrome c oxidase, a subunits of F0F1 ATPase, cytochrome b, a formyl peptide receptor (FPR) ligand, an N-formyl polypeptide, a caspase, a regulatory biomarker, such as, for example, cytochrome c, apoptosis-inducing factor, apoptotic protease activating factor, apoptotic protein activating factor-1, a second mitochondria-derived activator of caspase, a member of the bcl-2 family, direct IAP-binding protein, serine protease omi/HtrA2, or endonuclease G. The mitochondrial biomarker can be a nucleic acid that encodes any of the above polypeptides, or is capable of hybridizing to a nucleic acid that encodes any of the above polypeptides. In yet other embodiments, the mitochondrial biomarker is Cyt-C.

In certain embodiments, the presence or level of a biomarker in a sample can be measured by quantifying the amount of the biomarker in the sample as a whole molecule, as fragments of the biomarker, or by measuring the biomarker's activity in the sample or a derivative of the sample. Many biomarkers are polypeptides. Fragments of the biomarkers can be measured using a fragment that has an amino acid sequence which is unique to the biomarker in question. The fragment may be as few as 6 amino acids, although it may be 7, 8, 9, 10, 11, 12, 13, 14, 15 or more amino acids.

The method of this invention includes comparing a measured amount of the biomarker in the subject to a suitable reference source, as described elsewhere herein, wherein an increase in the amount of biomarker is indicative of ART toxicity or indicative of an increased risk of developing ART toxicity. For instance as presented elsewhere herein in the "Examples" section, a given Cyt-C reference value is used for establishing a threshold (e.g. Cyt-C>0.216 ng/ml) and any sample above this threshold is classified as exhibiting ART toxicity.

In one embodiment, the method of the present invention facilitates treatment decisions in a subject who is not currently undergoing ART treatment at the time of assessing for ART toxicity, but who will be treated with ART following assessment for ART toxicity. In some embodiments, the ART treatment is initiated after the sample to be analyzed in the context of the present invention has been obtained. In yet another embodiment, the therapy is initiated not more than 30 days, not more than 20 days, not more than 15 days, not more than 7 days or not more than 2 days, after said sample has been obtained.

In another embodiment, an increase in the amount of the biomarker as compared to the reference amount of the biomarker is an indication the ART should be adjusted or terminated in order to decrease or prevent ART toxicity.

In some embodiments, an increased of plasma Cyt-C level includes increases above the reference baseline level of 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween; as well as above a baseline level of 0.9-, 0.8-, 0.7-, 0.6-, 0.5-, 0.4-, 0.3-, 0.2-, or 0.1-fold, or less. In a specific embodiment, the increase can be at least 7 times more than the reference Cyt-C level, more specifically 7.9 times more (which is equivalent to more than 0.216 ng/ml).

In another embodiment, the method of the invention relies on assessing ART toxicity to facilitate the adoption of treatment strategies and the identification of preferred treatment schedules. In a particular embodiment, the level of Cyt-C in a sample from a subject is compared with the level of Cyt-C in a reference and an increase of Cyt-C level in the subject is indicative of whether or not ART treatment should be modified or terminated.

In a further embodiment, the extracellular concentration of Cyt-C in a tissue culture treated with antiretroviral drugs (i.e. Cyt-C taken from the culture supernatant) is used as an assay to predict drugs with propensity for causing mitochondrial toxicity and thus predict mitochondrial toxicity of antiviral agents in pre-clinical studies.

Quantitative Assays.

Determining the amount of biomarker (e.g. Cyt-C) or a fragment thereof refers to measuring the amount or concentration, preferably, semi-quantitatively or quantitatively of this peptide. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by any means in the art for determining the amount of a peptide or polypeptide in a sample. Such means comprise, but are not limited to, immunoassay devices and methods which may utilize labeled molecules in various sandwich, competition, or other assay formats. Such assays involve a signal which indicates the presence or absence of the peptide or polypeptide. Moreover, the signal strength can be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Such methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Determining the amount of a peptide or polypeptide may include the steps of (a) contacting the peptide with a specific ligand, (b) removing non-bound ligand, (c) measuring the amount of bound ligand. The bound ligand will generate an intensity signal. Binding according to the present invention includes both covalent and noncovalent binding. A ligand can be any compound, e.g., a peptide, polypeptide, antibody, nucleic acid, or small molecule, binding to the peptide or polypeptide described herein. Methods to prepare such ligands are well-known in the art. In certain embodiments, the ligand or agent binds specifically to the peptide or polypeptide of interest. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3, 5, 10, 20, 30, 40 or 50 times higher affinity than any other relevant peptide or polypeptide. Non-specific binding may be tolerable, if it can still be distinguished and measured unequivocally.

Binding of the ligand can be measured using any method known in the art. Some of theses methods could be, but are not limited to, the followings. Direct measurement (e.g. by NMR or surface plasmon resonance) or indirect measurement, if the ligand also serves as a substrate of an enzymatic activity of the peptide or polypeptide of interest, can be employed. In this later case, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal.

For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured. Additionally, the ligand may be coupled covalently or non-covalently to a label allowing detection and measurement of the ligand. Labeling may be done using direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. A secondary ligand may be coupled with a suitable label and/or be the target (receptor) of tertiary ligand binding to the secondary ligand. The use of secondary, tertiary or even higher order ligands is often used in the art to increase the signal. Suitable secondary and higher order ligands may include antibodies, secondary antibodies, and/or a streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-aminobenzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon, Oreg.). Also the use of quantum dots as fluorescent labels can be contemplated (Life technologies, Grand Island, N.Y.). Further methods known in the art such as protein microarrays (ProtoArray®, Life Technologies, Grand Island, N.Y.) SDS polyacrylamid gel electrophoresis (SDS-PAGE) or mass spectrometry can be used alone or in combination with labeling or other detection methods as described above.

In certain embodiment, an immunoassay is performed by contacting a sample from a subject to be tested with an appropriate antibody under conditions such that immunospecific binding can occur if the biomarker is present, and detecting or measuring the amount of any immunospecific binding by the antibody. The antibody may be contacted with the sample for at least about 10 minutes, 30 minutes, 1 hour, 3 hours, 5 hours, 7 hours, 10 hours, 15 hours, or 1 day. Any suitable immunoassay can be used, including, without limitation, competitive and non competitive assay systems using techniques such as western blots, radioimmunoassays, ELISA (enzyme linked immunosorbent assay) (e.g., eBioscience, San Diego Calif.; Bender MedSystems, Vienna Austria), "sandwich" immunoassays, immunoprecipitation assays, precipitation reactions, gel diffusion precipitation reactions, immunodiffusion assays, agglutination assays, complement fixation assays, immunoradiometric assays, fluorescent immunoassays and protein A immunoassays. Reference.

Reference amounts are calculated for a group of subjects based on the average or mean values for a given biomarker (e.g. Cyt-C) by applying standard statistically methods. In certain embodiments, the reference is computed from a group of control subjects that are under ART but without clinical evidence for ART-induced mitochondrial toxicity (ART-MT), In other embodiments, the reference is computed from a group of control subjects that are not treated by ART. In further embodiments, the ART-MT cases group are chosen so that they all meet case specific requirements such as being HIV positive with antibody test and having lactic acid >2 mmol/L). All control subjects are chosen so they match the age of the ART-MT cases group.

In one embodiment, the method of differentiating cases and controls and assessing a condition, or not, is best described by its receiver-operating characteristics (ROC) (Zweig et al., Clin. Chem., 1993, 39:561-577). The ROC graph is a plot of all of the sensitivity/specificity pairs resulting from continuously varying the decision threshold over the entire range of data observed. The clinical performance of a diagnostic method depends on its accuracy, i.e.

its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This can also be referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Dependent on a desired sensitivity and specificity for a diagnostic method, the ROC plot allows deriving suitable thresholds. Accordingly, the reference to be used for the aforementioned method of the present invention is based on establishing a ROC for a given group as described above and on deriving a threshold amount therefrom (i.e. a reference cut off value). This threshold allows to discriminate between subjects being susceptible ART toxicity from those which are not susceptible ART toxicity. It will be understood that an optimal sensitivity is desired for excluding a subject not being susceptible to ART Toxicity (i.e. a rule out) whereas an optimal specificity is envisaged for a subject to be assessed as being susceptible ART toxicity (i.e. a rule in). Furthermore, statistical approaches to estimate parameters of a linear model such as a generalized estimating equation (GEE) approach can be used to estimate the correlation between the outcomes.

Kit.

The invention includes a set of preferred antibodies, either labeled (e.g., fluorescer, quencher, etc.) or unlabeled, that are useful for the detection of at least the biomarker, Cyt-C.

In certain embodiments, a kit is provided. Commercially available kits for use in these methods are, in view of this specification, known to those of skill in the art. In general, kits will comprise a detection reagent that is suitable for detecting the presence of a polypeptide or nucleic acid, or mRNA of interest.

In one embodiment, a kit comprising an antibody to Cytochrome c (Cyt-C) is provided with instructions for use. In some embodiments, the kit is useful for measuring the level of Cyt-c in a sample from a subject having a viral infection. In other embodiments, the kit is useful for providing indication on presence or absence of antiretroviral therapy (ART) toxicity. In yet other embodiments, the kit is useful for providing recommendation of whether or not ART treatment should be modified or terminated in the subject.

In some embodiments, the kit includes a panel of probe sets or antibodies. Preferred probe sets are designed to detect the level of Cyt-C and provide information about the ART toxicity. Probe sets are particularly useful because they are smaller and cheaper than probe sets that are intended to detect as many peptides as possible in a particular genome. In the present invention, the probe sets are targeted to the detection of polypeptides that are informative about ART toxicity. Probe sets may also comprise a large or small number of probes that detect peptides that are not informative about ART toxicity. Such probes are useful as controls and for normalization (e.g., spiked-in markers). Probe sets may be a dry mixture or a mixture in solution. In some embodiments, probe sets can be affixed to a solid substrate to form an array of probes. The probes may be antibodies, or nucleic acids (e.g., DNA, RNA, chemically modified forms of DNA and RNA), LNAs (Locked nucleic acids), or PNAs (Peptide nucleic acids), or any other polymeric compound capable of specifically interacting with the peptides or nucleic acid sequences of interest. In other embodiments, the kit can be simply operated by the same subject that requires an ART toxicity check. In further embodiments, the kit can be a nanotechnology product and can be for single or multiple usages. Non-limiting examples of such products are kits for pregnancy test or for measuring glucose in the blood (e.g., Accu-Check Nano by Roche). In yet further embodiments, test results can be provided within a short timeline (i.e. few minutes or seconds).

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials and Methods

Pilot Case-Control Study:

Participants were Enrolled at Yale-New Haven Hospital from April, 2011 to March, 2013. Potential cases of ART-induced mitochondrial toxicity were identified by their primary HIV care providers. For the purposes of this study, a case was defined as HIV infected, treated with an NRTI based ART regimen for >12 months, and with clinical and/or laboratory evidence of one of the following ART toxicities: pancreatitis, peripheral neuropathy, lipodystrophy, creatinine >1.2 mg/dl, GFR <60 ml/min, cholesterol >199 mg/dl, and/or triglyceride >150 mg/dl. Each case was matched for age, race, and gender with an HIV-infected control, also treated with an NRTI based ART regimen for >12 months, but without ART toxicity. Demographic data and ART treatment history were obtained at enrollment. Each participant donated 20 cc of whole blood at the time of enrollment. Samples were centrifuged at 2000 rpm for 15 minutes (Prilutskii et al., Lab Delo, 1990, (2): p. 20-3). Plasma was removed and stored at −80° C. until use. The study protocol was approved by the Institutional Review Board of the Yale School of Medicine.

Cytochrome C Assay:

Samples were evaluated for the presence of Cyt-C using the Human Cytochrome C ELISA from Bender MedSystems (Vienna, Austria) according to manufacturer's instructions with slight modification. In brief, stored plasma samples were thawed at room temperature and centrifuged at 3000 rpm for 10 minutes to pellet any residual cellular debris. 100 µl of plasma was added to 20 µl of lysis buffer (ELISA kit) and allowed to incubate at room temperature for 1 hour. ELISA kit assay buffer was then added to each sample to achieve a 1:2 dilution of the plasma. 100 µl of each sample was loaded into each ELISA well in duplicate. The ELISA kit provided purified Human Cyt-C, which was freshly reconstituted and serially diluted (1:2) to create a standard for each experiment which was subjected to a 5-parameter curve fit (per manufacturer instructions). After application of TMB Substrate Solution (ELISA kit), microwells were incubated for 10 minutes at room temperature prior to the addition of the Stop Solution (ELISA). Final Cyt-C concentrations were read at 450 nm using a microplate reader (SpectraMAX, Molecular Devices, Sunnyvale, Calif.). Levels of Cyt-C were not affected by up to five freeze/thaw cycles per manufacturer report, which was verified in-house using a positive control sample. The limit of detection of the ELISA is 0.04 ng/mL.

Statistical Analysis:

Patient characteristics were summarized using descriptive statistics, such as medians, ranges, and percents. Cases and controls were compared using Wilcoxon Signed Rank test and McNemar test for continuous and categorical variables respectively. Spearman correlation coefficients were used to calculate the significance of associations between various patient characteristics and plasma Cyt-C concentrations. A receiver operator characteristics (ROC) curve was drawn to compare the sensitivity and 1-specificity of various Cyt-C concentration cutoffs for identifying cases. A GEE was used to evaluate the statistical significance of the difference in the proportion of cases and controls with plasma Cyt-C>0.216 ng/mL adjusted for duration of HIV infection, viral load, and CD4 count. Of note, the Cyt-C reference level of 0.216 ng/ml is equivalent to an increase of 7.9 times in Cyt-C level between the cases and controls. Statistical significance was established at alpha=0.05. All statistical tests were conducted using Prism 6.0 (GraphPad Software, Inc) and SAS 9.2 (Cary, N.C.).

The results of the experiments are now described in the following examples.

Example 1: Demographic and Clinical Characteristics of Study Participants

Twenty-one pairs of cases and controls were enrolled. Various characteristics of the study participants are presented in table 1. Each group contained 38% females, with a mean age of 53 (+/−7) years and was predominantly African American (71%), with 24% white non-Hispanic, and 5% Hispanic individuals. There was no difference between the groups with regards to CD4 count or viral load. Viral load was undetectable (<20 copies/mL) for 71% of cases and 86% of controls (p=0.45). In the GEE model, viral load was not correlated with Cyt-C levels. Past and present nucleoside/tide analogue exposure time was similar between the two groups (Table 1). Current nucleoside/tide analogues in use were Truvada (tenofovir/emtricitabine), Atripla (efavirenz/tenofovir/emtricitabine), Combivir (lamivudine/zidovudine), Epivir (lamivudine), and Trizir (abacavir/lamivudine/zidovudine). The use of an integrase inhibitor, protease inhibitor(s), and/or non-nucleoside/tide reverse transcriptase inhibitor was not correlated with plasma Cyt-C concentration (Mann-Whitney U test, p=0.99, 0.14, and 0.15, respectively). Duration of HIV infection was the only variable to differ significantly between the two groups, with controls having had the diagnosis of HIV for a longer period of time in years (15.4±7.3) than cases (8.4±4.6) (p<0.001); there was no significant correlation with plasma Cyt-C level (Spearman rho=−0.14, 95% CI 0.43, 0.18). The average duration of clinical and or laboratory abnormalities in the cases prior to attribution to ART was 4 years (±3.56 years). Forty-eight percent of the cases had two or more manifestations of toxicity. Duration of toxic symptoms had no correlation with plasma cyt-c concentration (Spearman rho=0.29, 95% CI −0.17-0.65). The cases had the following documented clinical manifestations of ART toxicity: hyperlipidemia (38%), elevated liver function tests (33%), thrombocytopenia (19%), elevated BUN/creatinine (19%), anemia (14%), lipodystrophy (14%), peripheral neuropathy (10%), lactic acidosis (5%), and pancytopenia (5%).

TABLE 1

Patients characteristics.
Table 1 presented below lists the demographic and clinical characteristics of study participants. P values were calculated using paired t-test for continuous variables and McNemar's test for categorical variables.

|  | HIV-infected with Toxicity (n = 21) % or mean (SD) | HIV-infected Controls (n = 21) % or mean (SD) | P Values |
|---|---|---|---|
| Gender |  |  | 1.00 |
| Female | 38.1% | 38.1% |  |
| Male | 61.9% | 61.9% |  |
| Age (Years) | 53.0 (+/−7.4) | 53.0 (+/−7.1) | 1.00 |
| Race |  |  | 1.00 |
| White non-hispanic | 23.8% | 23.8% |  |
| White hispanic | 4.8% | 4.8% |  |
| African American | 71.4% | 71.4% |  |
| CD4+ T-cell Count | 602 (+/−388) | 750 (+/−257) | 0.16 |

TABLE 1-continued

Patients characteristics.
Table 1 presented below lists the demographic and clinical characteristics of
study participants. P values were calculated using paired t-test for continuous variables and
McNemar's test for categorical variables.

|  | HIV-infected with Toxicity (n = 21) % or mean (SD) | HIV-infected Controls (n = 21) % or mean (SD) | P Values |
|---|---|---|---|
| Viral Load |  |  |  |
| % undetectable | 71.4% | 85.7% | 0.45 |
| average viral load (copies/mL) | 5296 (+/−11769) § | 5966 (+/−10248) | 0.69 |
| Duration of HIV infection (years) | 8.4 (+/−4.59) | 15.4 (+/−7.30) | 0.0005* |
| Currently on Nucleoside Analog | 100.00% | 100.00% | 1.00 |
| Truvada | 57.1% | 38.1% |  |
| Atripla | 14.3% | 42.9% |  |
| Combivir | 4.8% | 0.0% |  |
| Epivir | 23.8% | 14.3% |  |
| Trizir | 0.0% | 4.8% |  |
| Previous Nucleoside Analog Exposures | 71.4% | 66.7% | 0.73 |
| More than one previous nucleoside | 33.3% | 52.4% | 1.00 |
| No previous nucleoside exposure | 28.6% | 33.3% | 1.00 |
| Total duration of Nucleoside exposure | 7.2 (+/−4.69) | 7.9 (+/−3.55) | 0.62 |
| Current exposure to protease inhibitor | 19.0% | 4.8% | 0.25 |
| Current exposure to protease inhibitor | 66.7% | 33.3% | 0.09 |
| Current exposure to NNRTI | 38.1% | 61.9% | 0.23 |

SD: standard deviation;
*statistically significant;
§ Cases n = 6 and HIV-positive control n = 3

Example 2: Plasma Cyt-C Statistics Between Cases and Controls

The results presented herein demonstrate that the level of Cyt-C in the plasma of HIV patients is statistically different between subjects experiencing or not HAART toxicity.

Figure 1:
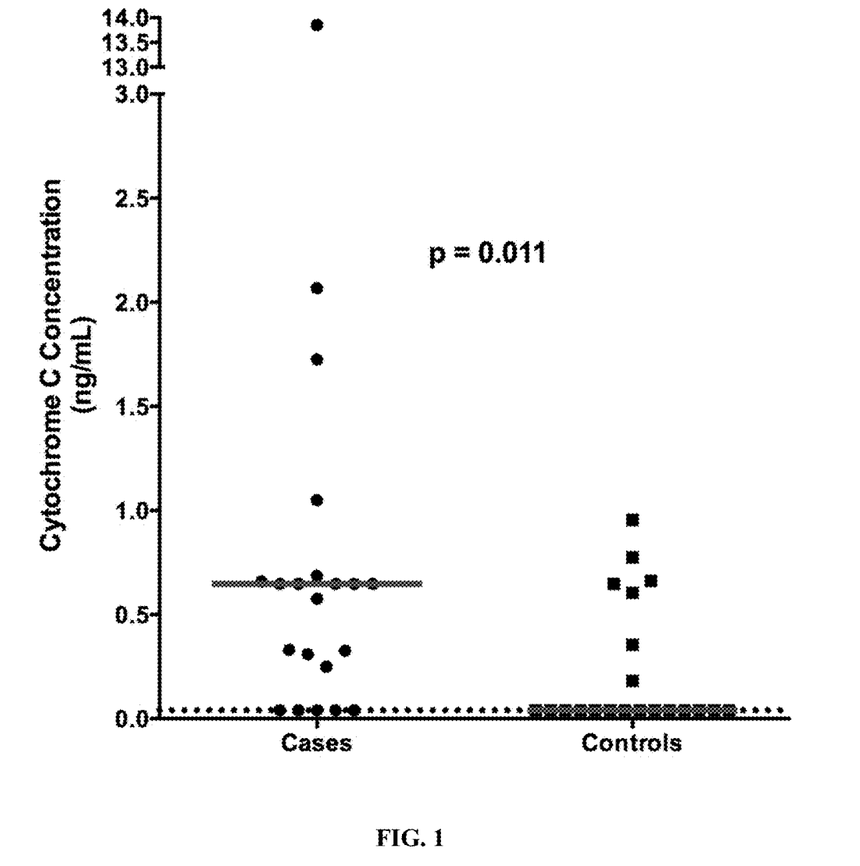
FIG. 1 is a graph illustrating the absolute plasma Cyt-C concentration in HIV-infected individuals with and without ART-induced mitochondrial toxicity. The solid gray horizontal lines represent the median Cyt-C concentrations for the cases and controls respectively. The dotted horizontal line represents the limit of detection for the ELISA: 0.04 ng/mL. The significance of the difference between the two groups was evaluated using Wilcoxon Signed Rank test. When the analysis was run omitting the outlier from the cases, along with its matched counterpart in the HIV positive control group, the significance remained with $p<0.02$.
Figure 2:
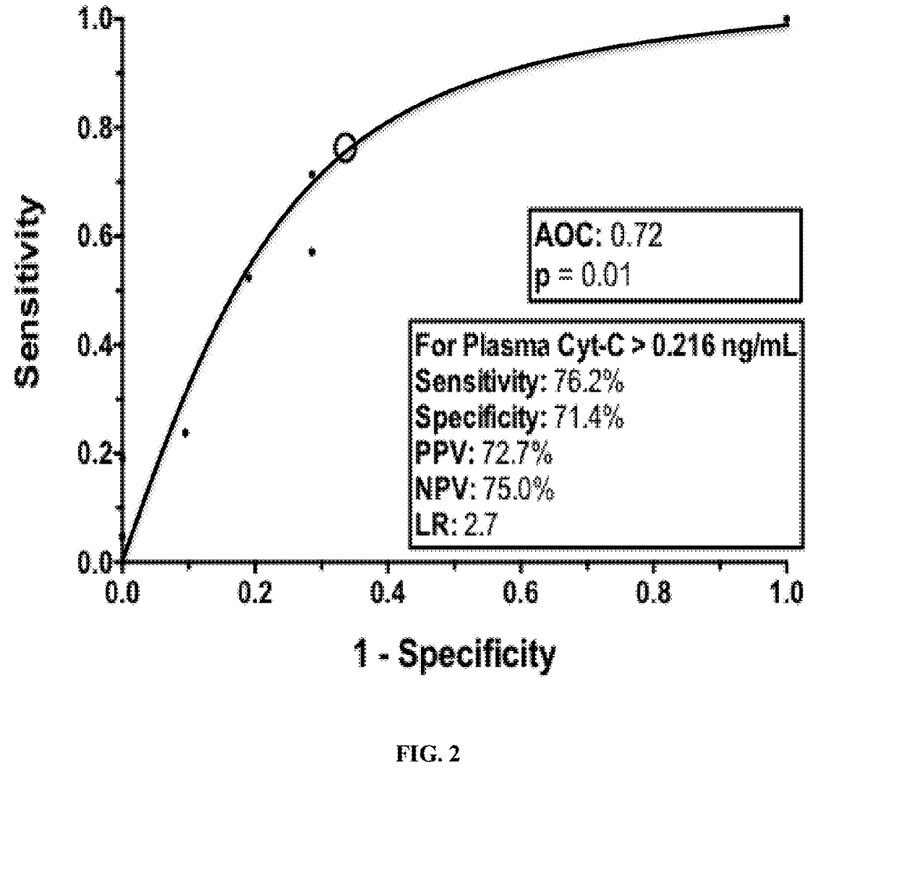
FIG. 2 is a graph representing the Receiver Operator Characteristic Curve (ROC) for plasma Cyt-C in HIV-infected individuals. For Cyt-C Concentration >0.216 ng/mL (reference value): Sensitivity 95% CI 0.52 to 0.91; Specificity 95% CI 0.47 to 0.88; PPV: positive predictive value with 95% CI 0.50 to 0.89; NPV: negative predictive value with 95% CI 0.51 to 0.90; LR: Likelihood Ratio. When the analysis was run without the outlier case and its matched control, the sensitivity and specificity of plasma Cyt-C>0.216 ng/mL to detect cases became 75.0% (95% CI 0.51, 0.91) and 75.0% (95% CI 0.51, 0.91) respectively. Area under the curve: 0.72 (p=0.01)
Figure 3:
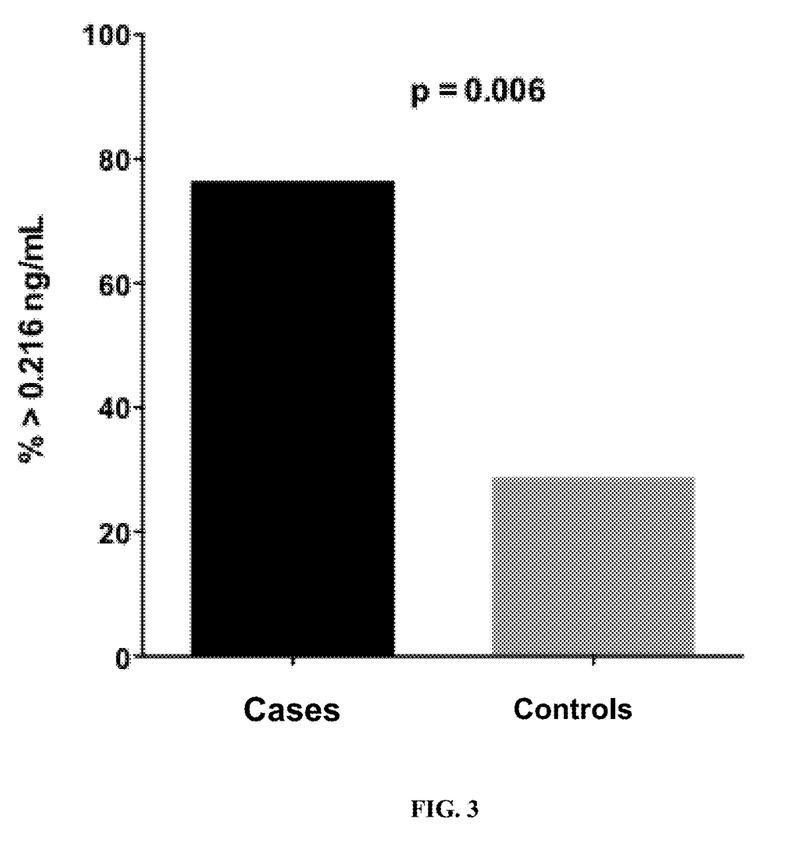
FIG. 3 is a histogram illustrating the proportion of HIV-infected individuals with plasma Cyt-C concentrations above the chosen reference value of 0.216 ng/mL: P value calculated using McNemar test with 95% confidence interval of 0.01 to 0.85. The generalized estimating equations (GEE) approach demonstrated an odds ratio of 7.86 in favor of cases with 95% CI 0.02 to 0.39 (p=0.01).

The difference in the median plasma concentration of Cyt-C was statistically significant between cases (0.65 ng/mL, range <0.04-3.85) and controls (<0.04 ng/mL, range <0.04-0.95, p<0.01) (FIG. 1). Using the ROC approach, plasma Cyt-C concentration of >0.216 ng/mL had a sensitivity of 76.2% (95% CI 0.52, 0.91) and a specificity of 71.4% (95% CI 0.47, 0.88) to detect the cases (FIG. 2). Using >0.216 ng/mL of plasma Cyt-C as the definition and reference value of a positive result, a significantly higher proportion of cases (76.2%) than controls (28.6%) had a positive result (McNemar test, p<0.01, 95% CI=0.01-0.85) (FIG. 3). In addition, once the duration of HIV infection, viral load, and CD4 count were adjusted using the GEE approach, the odds ratio were 7.86 (95% CI 1.57, 39.20) for cases to have a plasma level of Cyt-C>0.216 ng/mL compared with controls (p=0.01). Furthermore, when the single outlier case and its matched control were removed from analysis, the difference in Cyt-C plasma concentration remained significant between the two groups (p<0.02).

Example 3: Plasma Cyt-C as a Biomarker for ART-Induced Mitochondrial Toxicity in HIV-Infected Patients on HAART The present invention is the first to examine the utility of plasma Cyt-C as a biomarker of ART-induced mitochondrial toxicity in HIV infected patients on ART. Various concentration cutoffs of Cyt-C were analyzed to determine which might be the best combinations of sensitivity and specificity, should it be used as a clinical test. No study to date has reported these test characteristics for plasma Cyt-C in any disease state. Only one study using a mouse model of drug induced hepatic toxicity has demonstrated serum levels of 50 to 150 ng/mL of Cyt-C, with the saline treated controls demonstrating levels of 0 to 50 ng/mL, as measured by ELISA (Miller et al., *J Appl Toxicol* 2008, 28:815-828). In this and other drug toxicity studies, medications were being given with the intention of inducing high levels of cellular death, which may explain why the Cyt-C concentrations were higher than those seen in the present invention.

In conclusion, the invention presented herein demonstrates that elevated plasma Cyt-C is a reliable biomarker for ART-induced mitochondrial toxicity in HIV-infected patients on HAART. Plasma Cyt-C can be detected using a commercially available ELISA. In the examples presented herein, the best balance of sensitivity and specificity was achieved using a plasma Cyt-C reference concentration cut off of >0.216 ng/mL. Collection of plasma for ELISA is less invasive, inexpensive, and technically simple, especially compared with tissue biopsy. Therefore, Plasma Cyt-C is an excellent biologic marker for ART toxicity. Furthermore, plasma Cyt-C could also be used as an ideal monitoring tool in the HIV-infected population receiving HAART.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for detecting antiretroviral drug toxicity in a subject having a viral infection, the method comprising:
   i. detecting a level of Cytochrome c (Cyt-C) in a plasma sample from the subject;
   ii. determining that the subject has antiretroviral drug toxicity when the level of Cyt-C in the plasma sample from the subject is at least 2 times more than the level of Cyt-C in a baseline reference; and,
   iii. administering a modified level of antiretroviral treatment to the subject having been determined to have antiretroviral drug toxicity.

2. The method of claim 1, wherein the toxicity is a mitochondrial toxicity.

3. The method of claim 1, wherein the viral infection is a retroviral infection.

4. The method of claim 3, wherein the retroviral infection is a human immunodeficiency virus (HIV) infection.

5. The method of claim 1, wherein the antiretroviral drug is at least one selected from the group consisting of nucleotide reverse transcriptase inhibitor (NTRTI), nucleoside reverse transcriptase inhibitor (NRTI), protease inhibitor (PI) and integrase nuclear strand transfer inhibitor (INSTI).

6. The method of claim 1, wherein the antiretroviral drug is a highly active antiretroviral therapy (HAART).

7. The method of claim 1, wherein determining the level of the Cyt-C is accomplished using at least one technique selected from the group consisting of ELISA, spectrophotometry and protein microarray.

8. The method of claim 1, wherein the subject is a mammal.

9. The method of claim 8, wherein the mammal is a human.

10. The method of claim 9, wherein the human is a child.

11. The method of claim 1, wherein step ii comprises determining that the subject has antiretroviral drug toxicity when the level of Cyt-C in the plasma sample from the subject is at least 7 times more than the level of Cyt-C in a baseline reference.

12. A method for assessing toxicity associated with an antiretroviral therapy (ART) in a subject having a viral infection as a means to modify or terminate the ART treatment, the method comprising:
   i. detecting a level of Cytochrome c (Cyt-C) in a plasma sample from the subject;
   ii. determining that the subject has ART toxicity when the level of Cyt-C in the plasma sample is at least 2 times more than the level of Cyt-C in a baseline reference, and
   iii. administering a modified level of ART treatment to the subject having been determined to have ART toxicity.

13. The method of claim 12, wherein the toxicity is a mitochondrial toxicity.

14. The method of claim 12, wherein the viral infection is retroviral infection.

15. The method of claim 14, wherein the retroviral infection is a human immunodeficiency virus (HIV) infection.

16. The method of claim 12, wherein the ART is at least one selected from the group consisting of nucleotide reverse transcriptase inhibitor (NTRTI), nucleoside reverse transcriptase inhibitor (NRTI), protease inhibitor (PI) and integrase nuclear strand transfer inhibitor (INSTI).

17. The method of claim 12, wherein the ART is a highly active antiretroviral therapy (HAART).

18. The method of claim 12, wherein determining the level of the Cyt-C is accomplished using at least one technique selected from the group consisting of ELISA, spectrophotometry and protein microarray.

19. The method of claim 12, wherein the subject is a mammal.

20. The method of claim 19, wherein the mammal is a human.

21. The method of claim 20, wherein the human is a child.

22. The method of claim 12, wherein step ii comprises determining that the subject has ART when the level of Cyt-C in the plasma sample from the subject is at least 7 times more than the level of Cyt-C in a baseline reference.

* * * * *